(12) United States Patent
Okuda et al.

(10) Patent No.: US 9,565,993 B2
(45) Date of Patent: Feb. 14, 2017

(54) ENDOSCOPE

(71) Applicants: PIONEER CORPORATION, Kanagawa (JP); NATIONAL CENTER FOR CHILD HEALTH & DEVELOPMENT, Tokyo (JP)

(72) Inventors: Yoshiyuki Okuda, Kanagawa (JP); Hiroshi Yokota, Kanagawa (JP); Toshio Chiba, Tokyo (JP); Hiromasa Yamashita, Tokyo (JP)

(73) Assignees: PIONEER CORPORATION, Kanagawa (JP); NATIONAL CENTER FOR CHILD HEALTH AND DEVELOPMENT, Tokyo (JP)

( * ) Notice: Subject to any disclaimer, the term of this patent is extended or adjusted under 35 U.S.C. 154(b) by 144 days.

(21) Appl. No.: 14/401,567

(22) PCT Filed: May 10, 2013

(86) PCT No.: PCT/JP2013/003008
§ 371 (c)(1),
(2) Date: Nov. 17, 2014

(87) PCT Pub. No.: WO2013/172005
PCT Pub. Date: Nov. 21, 2013

(65) Prior Publication Data
US 2015/0157194 A1    Jun. 11, 2015

(30) Foreign Application Priority Data
May 17, 2012 (JP) ................................. 2012-113386

(51) Int. Cl.
A61B 1/04    (2006.01)
A61B 1/06    (2006.01)
(Continued)

(52) U.S. Cl.
CPC ....... A61B 1/00197 (2013.01); A61B 1/00096 (2013.01); A61B 1/00165 (2013.01);
(Continued)

(58) Field of Classification Search
CPC ......... A61B 1/00197; A61B 1/04; A61B 1/07; A61B 1/0684; A61B 1/042; A61B 1/055; A61B 1/0669
(Continued)

(56) References Cited

U.S. PATENT DOCUMENTS 6,063,024 A    5/2000  Yamamoto
2008/0269563 A1  10/2008  Takahashi

FOREIGN PATENT DOCUMENTS

| JP | 06-250104 | 9/1994 |
| JP | 08-152568 | 6/1996 |
| JP | 2008-289863 | 12/2008 |

OTHER PUBLICATIONS

International Search Report PCT/JP2013/003008 dated Aug. 6, 2013.

*Primary Examiner* — Timothy J Neal
(74) *Attorney, Agent, or Firm* — Yoing & Thompson

(57) ABSTRACT

The object lens 21 and the ocular lens 22 are disposed in the lens barrel unit 11 and the relay lens system 23 is disposed therebetween. The image sensor 31 is disposed in the camera unit 12 and the coaxial illumination unit 32 is disposed therearound. The focus position shift member 25 is disposed at the image formation position L1 in the lens barrel unit 11. The light from the coaxial illumination unit 32 is imaged at the image formation position L1 and is shifted to a position L2 by the focus position shift member 25. Since the position L2 positions at a position closer than a focus position, light through the object lens 21 diffuses to illuminate the object 51.

5 Claims, 5 Drawing Sheets

(51) Int. Cl.
*A61B 1/00* (2006.01)
*G02B 23/24* (2006.01)
*A61B 1/07* (2006.01)
*A61B 1/055* (2006.01)

(52) U.S. Cl.
CPC ............ *A61B 1/00188* (2013.01); *A61B 1/04* (2013.01); *A61B 1/055* (2013.01); *A61B 1/0607* (2013.01); *A61B 1/07* (2013.01); *G02B 23/2446* (2013.01); *G02B 23/2461* (2013.01); *A61B 1/0684* (2013.01)

(58) Field of Classification Search
USPC ................. 600/109, 160, 130, 138, 176–180
See application file for complete search history.

F I G. 2
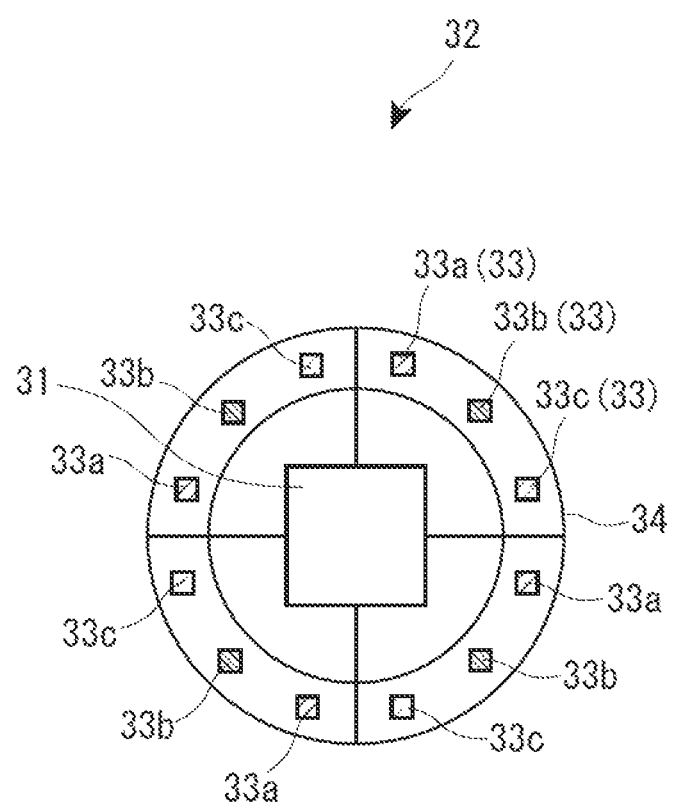

ENDOSCOPE

TECHNICAL FIELD

The present invention relates to an endoscope which is used for inserting a body cavity and for observing an organ and the like, and more specifically, relates to a rigid endoscope.

BACKGROUND ART

A rigid endoscope having a relay optical system has been known as this kind of endoscope (see Patent Document 1).

The rigid endoscope has a cylindrical insertion unit made of a rigid member, a relay optical system (relay lens system) provided in the insertion unit, an observation unit provided at a base end portion of the relay optical system, two light guide optical fiber bundles provided with the relay optical system in the insertion unit and a light source device connected to a base end of the two light guide fiber bundles.

The light source device is activated, and illumination light from the light source device is guided by the light guide fiber bundles and is illuminated on an object (examined body) as observation target from a tip end thereof. Reflected light from the examined body forms images at the observation unit and the images are observed by the naked eyes through the observation unit.

[Patent Document 1] JP 2007-133175A

DISCLOSURE OF THE INVENTION

Problems that the Invention is to Solve

In such a known rigid endoscope, since the light from the external light source device is guided by the light guide fiber bundles (optical fiber) into the body, an illumination optical path for guiding the light by the optical fiber is provided in the insertion unit in addition to an imaging optical path transmitting image light of the examined body by the relay lens system. Therefore, this makes the outer diameter of the insertion unit (lens barrel unit) including the relay lens system extremely larger, leading to great burden to patients. In this case, though it is conceivable that the outer diameter of the lens barrel unit is made small, in association with it, if the imaging optical path is made narrower, the diameter of the relay lens system also becomes smaller, resulting in light volume loss in the relay lens system. Further, since the imaging optical path is separately provided from the illumination optical path, a device structure becomes complex and the light guide fiber bundles are cumbersome to handle, and handling therefor is difficult.

An advantage of the invention is to provide an endoscope which can illuminate the object with sufficient light volume and can have a smaller outer diameter of the lens barrel unit.

Means for Solving the Problems

The present invention provides an endoscope comprising: a lens barrel unit that has a relay lens system; a camera unit that is connected to a base end side of the lens barrel unit and has an imaging device imaging an object through the relay lens system; a coaxial illumination unit that is disposed to surround an imaging device and illuminates the object through the relay lens system; and an optical path reduction device that is disposed at one of a plurality of image formation positions in the relay lens system and reduces an effective optical path of the coaxial illumination unit to the object.

According to this configuration, the effective optical path of the coaxial illumination unit to the object is reduced by the optical path reduction device. Therefore, illumination images of the coaxial illumination unit can be shifted with respect to an intermediate image surface formed at a front and a back of the relay lens system or between lens units constituting the relay lens system. As a result, illumination light is not focused at a position of the object, and thus the object can be properly illuminated. In other words, the object can be illuminated with sufficient light volume, and the reduced sensitivity of the imaging device can be avoided. Further, since the coaxial illumination unit can be accommodated in the camera unit, an imaging optical path transmitting the image light of the object and an illumination optical path guiding illumination can be used commonly. As a result, the outer diameter of the lens barrel unit can be formed in conformity with the outer diameter of the relay lens system and can be made narrower than that of a known endoscope.

In this case, it is preferable that the lens barrel unit further has an object lens ahead of the relay lens system, and the optical path reduction device is disposed between a most-advanced lens unit and the object lens such as to include a space in front of a backward focus position of the object lens.

According to this configuration, the illumination light illuminating the object can be efficiently diffused while light volume loss is restrained. In order to properly diffuse the illumination light, it is preferable that the optical path reduction device is positioned ahead of (on an object side) the intermediate image surface of the most-advanced lens unit.

In addition, it is preferable that the optical path reduction device has a bundle fiber in a cross-sectional shape corresponding to a light-emitting surface of the coaxial illumination unit.

Likewise, it is preferable that the optical path reduction device has a light guide in a cross-sectional shape corresponding to a light-emitting surface of the coaxial illumination unit, and of which refractive index is more than 1.

According to these configurations, the effective optical path of the coaxial illumination unit to the object can be reduced by an extremely simple structure.

On the other hand, it is preferable that the coaxial illumination unit has a ring-shaped light-emitting diode array having a plurality of light-emitting diodes mixed with at least three primary colors.

According to this configuration, the object can be imaged in color.

BRIEF DESCRIPTION OF THE DRAWINGS

FIG. 2 is a diagram of a coaxial illumination unit in the rigid endoscope seen from a front side.

DESCRIPTION OF EXEMPLARY EMBODIMENTS

A rigid endoscope applied with an endoscope according to one embodiment of the invention will be explained with reference to accompanying drawings. The rigid endoscope is configured to be inserted into a body cavity to image affected area (object) incurred in organs.

Figure 1:
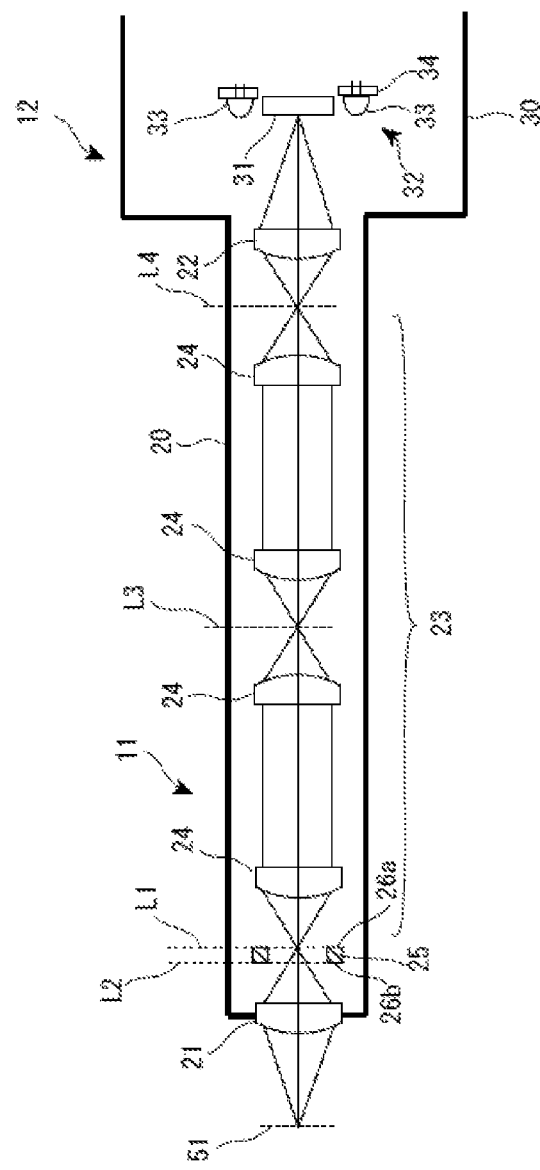
FIG. 1 is a diagram illustrating a structure of a rigid endoscope according to the first embodiment.

FIG. 1 is a diagram of a rigid endoscope 1 having, as illustrated in FIG. 1, a lens barrel unit 11 which is inserted in the body cavity, a camera unit 12 connected to a base end of the lens barrel unit 11 and imaging an object 51 through the lens barrel unit 11, and a coaxial illumination unit 32 installed in the camera unit 12 and illuminates the object 51 through the lens barrel unit 11.

The lens barrel unit 11 is a portion to be inserted inside a human body, and has a cylindrical body 20 of a rigid cylindrical member, an object lens 21 disposed at a tip end of the cylindrical body 20, an ocular lens 22 disposed at a base end of the cylindrical body 20, and a relay lens system 23 having a plurality of lens units 24 disposed between the object lens 21 and the ocular lens 22 in the cylindrical body 20. The object lens 21 forms light images of the object 51 as observation target. The relay lens system 23 transmits the light images formed by the object lens 21 to the ocular lens 22 at the base end side. The ocular lens 22 forms the light images of the object on an image sensor 31 of the camera unit 12 described later.

Further, the lens barrel unit 11 includes a focus position shift member (optical path reduction device) 25 positioned between the most-advanced lens unit 24 and the object lens 21. The focus position shift member 25 has a function to shift a focus position of illumination light from the coaxial illumination unit 32 (a detail thereof will be explained later).

The illumination light from the coaxial illumination unit 32 illuminates the object 51 through the ocular lens 22, the relay lens system 23, the focus position shift member 25 and the object lens 21. While, image light reflected from the object 51 forms images on an imaging area of the image sensor 31 through the object lens 21, the relay lens system 23 and the ocular lens 22.

The camera unit 12 is connected to the base end of the lens barrel unit 11 and is composed of the image sensor 31 accommodated in a housing 30. The image sensor 31 is, for example, composed of a HEED (High-efficiency Electron Emission Device)-HARP (High-gain Avalanche Rushing amorphous Photoconductor), a CCD (Charge Coupled Device), a CMOS (Complementary MOS) or the like.

Further, the coaxial illumination unit 32 is disposed in the housing 30 of the camera unit 12 to surround the image sensor 31.

As illustrated in FIGS. 1 and 2, the coaxial illumination unit 32 forms a light source illuminating the object 51, and has a ring-shaped illumination substrate 34 disposed to surround the image sensor 31 and a plurality of LEDs (Light Emitting Diode) 33 mounted on the illumination substrate 34. Shortly, the plurality of LEDs 33 are circularly disposed to surround the image sensor 31 on the illumination substrate 34. The plurality of LEDs 33 in the embodiment are disposed at regular intervals in a circumferential direction to form four groups, each of which having three primary colors of red, green and blue LEDs 33a, 33b and 33c.

In this case, in the rigid endoscope 1 of the embodiment, a time sequential process is performed, in which imaging processes for red color, blue color and green color are performed by time division, and color image views are generated by image composition.

Figure 3:
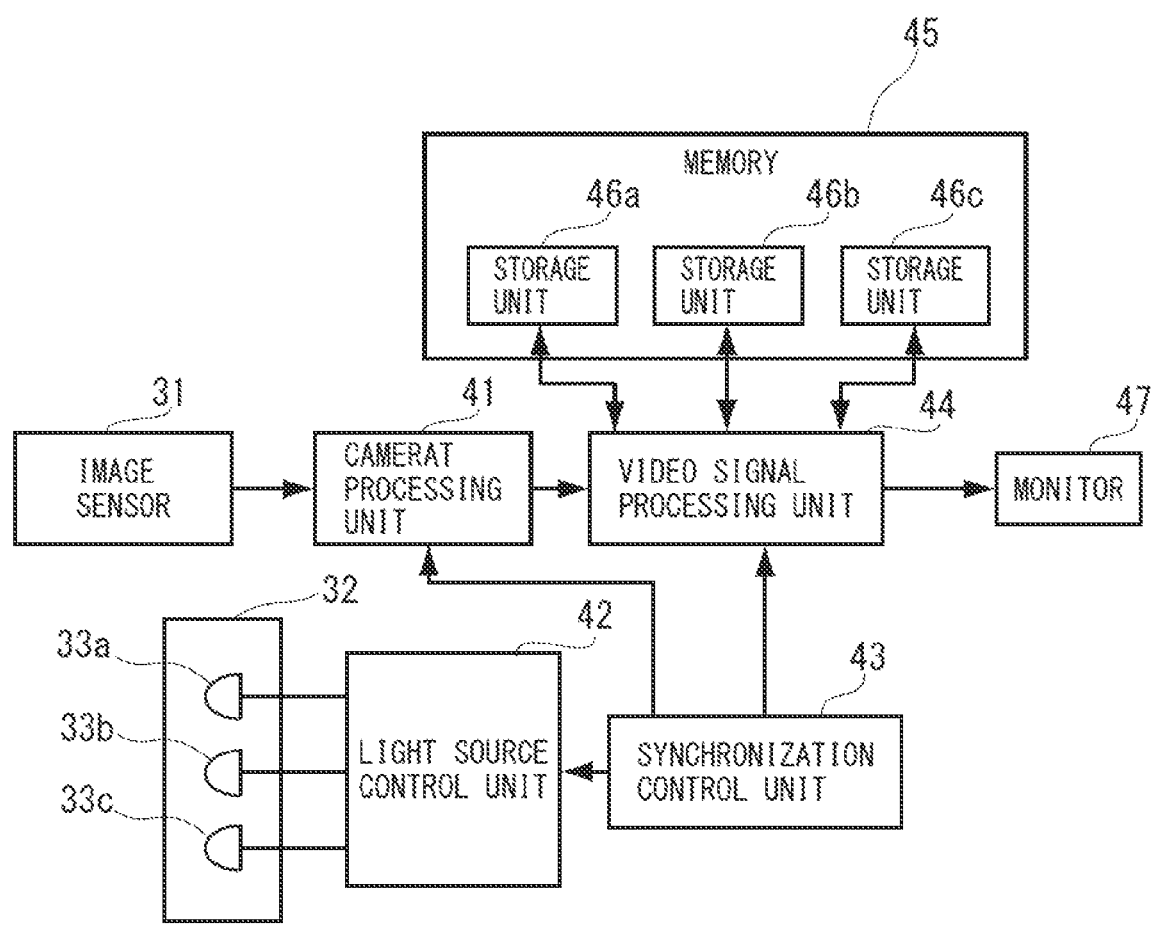
FIG. 3 is a block diagram of an image processing circuit in the rigid endoscope.

FIG. 3 illustrates a structure of an imaging processing circuit of the rigid endoscope 1. As illustrated in FIG. 1, the image processing circuit has a camera process unit 41, a light source control unit 42, a synchronization control unit 43 and a video signal processing unit 44.

The camera processing unit 41 processes imaging signals from the image sensor 31. The light source control unit 42 controls lighting of LEDs 33a, 33b and 33c of each color constituting the coaxial illumination unit 32. The synchronization control unit 43 sends synchronization signals to the camera processing unit 41, the video signal processing unit 44 and the light source control unit 42 and controls synchronization of camera images with the coaxial illumination unit 32. The video signal processing unit 44 processes imaging signals from the camera process unit 41 to output component color video signals. The video signal process unit 44 has a memory 45. The memory 45 has storage areas 46a, 46b and 46c, each of which storing image signals of each color of red, blue and green. Further, a monitor 47 is provided for the video signal process unit 44. The respective LEDs 33a, 33b and 33c of red color, blue color and green color are turned on in a predetermined order by the light source control unit 42 in synchronization with the synchronization signals from the synchronization control unit 43.

The image sensor 31 performs photoelectric conversion on the image light from the object 51 and outputs imaging signals corresponding to the image light from the object 51. The imaging signals are transmitted to the video signal processing unit 44 through the camera processing unit 41. Further, the video signal processing unit 44 has the memory 45 which stores imaging signals of each color of red, blue and green. The imaging signals from the image sensor 31 are sequentially stored in the storage areas 46a, 46b and 46c of the memory 45 in synchronization with the synchronization signals from the synchronization control unit 43.

Actual actions in detail are as follows: the red color LEDs 33a of the coaxial illumination unit 32 are turned on during red image signal generation period and the imaging signals from the image sensor 31 are stored in the storage area 46a. The green color LEDs 33b are turned on during green image signal generation period and the imaging signals from the image sensor 31 are stored in the storage area 46b. The blue color LEDs 33c are turned on during blue imaging signal generation period and the imaging signals from the image sensor 31 are stored in the storage area 46c.

Thus, the image signals of the red color captured images are stored in the storage area 46a of the memory 45, the image signals of the green color captured images are stored in the storage area 46b, and the image signals of the blue color captured image are stored in the storage area 46c. The video signal process unit 44 synthesizes the image signals of each color of red, green and blue stored in these storage areas 46a, 46b and 46c and generates the component color video signals. The component color video signals are transmitted to the monitor 47 to display colored video images of the object as observation target.

Figure 4:
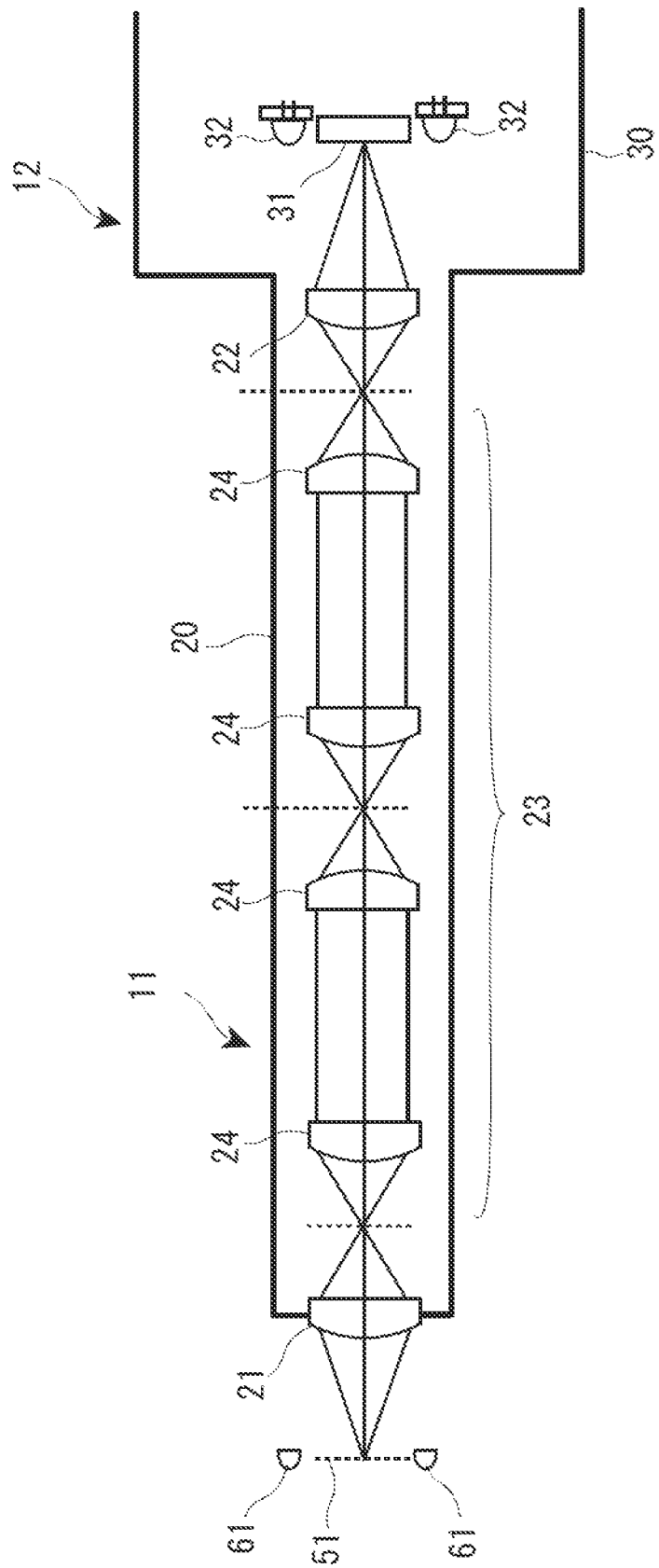
FIG. 4 is an image formation diagram without a focus position shift member in the rigid endoscope.

As illustrated in FIG. 4, when the coaxial illumination unit 32 is arranged in the housing 30 of the camera unit 12, the light from the coaxial illumination unit 32 is illuminated through the ocular lens 22, the relay lens system 23 and the object lens 21 and is optically affected by these lenses. Shortly, in the structure where the coaxial illumination unit 32 is arranged around the image sensor 31, the coaxial illumination unit 32 forms images around the object 51 with optical influence by these lenses, by which the object 51 cannot be illuminated (the object 51 itself becomes extremely dark).

Then, in the embodiment, the focus position shift member 25 is disposed in the lens barrel unit 11.

Figure 5:
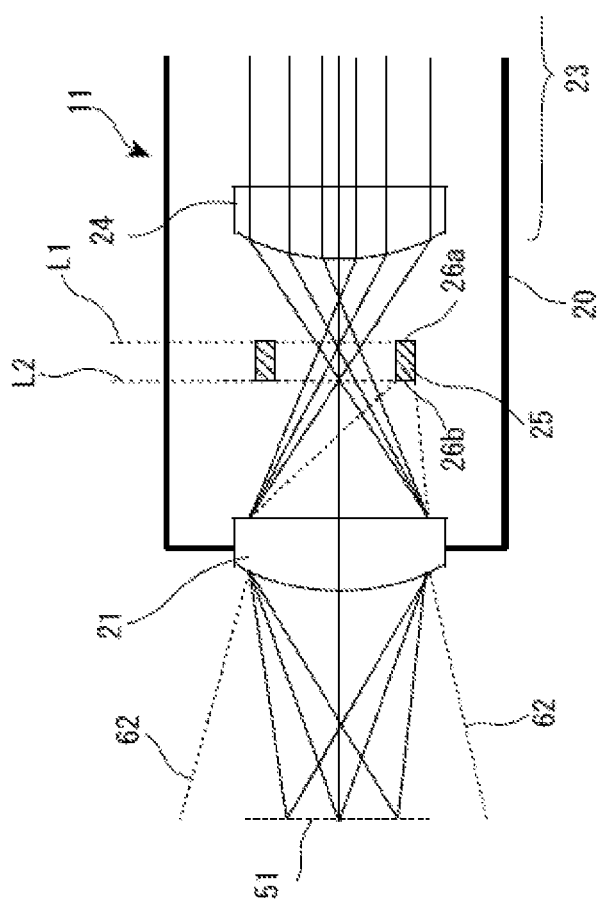
FIG. 5 is an explanatory view of a function of the focus position shift member in the rigid endoscope.

As illustrated in FIGS. 1 and 5, in the rigid endoscope 1 of the embodiment, the coaxial illumination unit 32 is disposed in the housing 30 of the camera unit 12, and the illumination light from the coaxial illumination unit 32 is illuminated on the object 51 through the ocular lens 22, the relay lens system 23, the focus position shift member 25 and the object lens 21. In this case, an optical path (illumination optical path) of the illumination light in which the light from the coaxial illumination unit 32 is illuminated on the object 51 as observation target is as the same as an imaging optical path of the object 51 reaching from the object 51 to the image sensor 31 through the object lens 21, the relay lens system 23 and the ocular lens 22.

Therefore, the focus position shift member 25 is disposed such that the coaxial illumination unit 32 does not form images around the object 51. The focus position shift member 25 is disposed at a position corresponding to a position L1 of a first image formation surface between the object lens 21 and a front end of the relay lens system 23 in the lens barrel unit 11. The focus position shift member 25 is formed in a hollow cylindrical shape so as not to effect on the imaging optical path. For example, the bundle fiber (optical fiber bundle) is used for the focus position shift member 25, in which a plurality of optical fibers oriented to the same optical axis direction are bundled cylindrically.

FIG. 5 illustrates the optical path of the light from the coaxial illumination unit 32 when the focus position shift member 25 is arranged. As illustrated in FIG. 1, the light from the coaxial illumination unit 32 forms images at the position L1 (intermediate image surface) through the ocular lens 22 and the relay lens system 23, and (a surface at the base end side of) the focus position shift member 25 is arranged at the position L1. Therefore, the formed image light comes from an illumination incident surface 26a at one side of the focus position shift member 25, is shifted by the focus position shift member 25, and is output from an illumination output surface 26b at the other side of the focus position shift member 25. Thus, an intermediate image from the coaxial illumination unit 32 is equivalent to the image formed on the illumination output surface 26b of the focus position shift member 25.

A position L2 of the illumination output surface 26b positions closer to the object lens 21 than a focus position of the object lens 21. An image positioned closer than the focus position of the object lens 21 diffuses without being formed an image by the object lens 21. Therefore, as illustrated by light rays 62 in FIG. 5, the light output from the illumination output surface 26b of the focus position shift member 25 is diffused through the object lens 21 and illuminates the object 51.

Thus, when the focus position shift member 25 is disposed at the position L1 of the image formation surface of the light from the coaxial illumination unit 32 in the lens barrel unit 11, the intermediate image from the coaxial illumination unit 32 comes at the position L2 closer than the focus position of the object lens 21, and the light from the coaxial illumination unit 32 arranged around the image sensor 31 is output from the object lens 21 to be diffused, thereby the object 51 can be illuminated sufficiently.

As explained above, in the rigid endoscope 1 of the embodiment, the coaxial illumination unit 32 (light source) is provided in the housing 30 of the camera unit 12, and the imaging optical path transmitting the image light of the object image and the illumination optical path guiding the illumination are used commonly. Therefore, the outer diameter of the lens barrel unit 11 can be smaller, leading to reduction of burden to patients.

Further, by commonly using the imaging optical path transmitting the image light of the object image and the illumination optical path guiding the illumination, the outer diameter of the lens barrel unit 11 can be smaller, which means that there is no need to make the outer diameter of the relay lens system 23 smaller. Therefore, light volume loss in the relay lens system 23 is restrained and reduced sensitivity of the camera unit 12 can be avoided. Still further, since the illumination optical path for guiding the illumination from the outside to the tip end of the lens barrel unit 11 is not necessary, the tip end of the lens barrel unit 11 can have a simple shape only with the object lens 21. Therefore, medical solution can spread substantially when the device is antisepticised, resulting in killing remaining germs.

The invention is not limited to the embodiment above and various modifications and applications can be adapted in a range without departing from the scope of the invention. For example, in the above embodiment, though the focus position shift member 25 is structured with the optical fiber bundle, the invention is not limited thereto. Any type of the focus position shift member 25 can be used only if the above focus position of the illumination light is shifted.

In other words, an optical guiding member (light guide) having refraction index more than 1 as the focus position shift member 25 may be used in place of the optical fiber bundle. The transparent focus position shift member 25 structured with the optical guiding member having refraction index more than 1 as such may be formed by glass or a synthetic resin. In case that a medium which is transparent and of which the refractive index is N is used as the focus position shift member 25, the focus position shift volume depending on the distance L between the illumination incident surface 26a and the illumination output surface 26b of the focus position shift member 25 is set to (L−L/N).

Further, the illumination output surface 26b of the above focus position shift member 25 may not be flat, but may have a convexo-concave shape to easily diffuse the light. Still further, the illumination output surface 26b of the focus position shift member 25 may be formed in a corrugated shape.

While, in the above embodiment, though the focus position shift member 25 is arranged at the position L1 of the first image formation surface closest to the object lens 21 side in the lens barrel unit 11, the light image of the coaxial illumination unit 32 is formed at a front and a back of the relay lens system 23 or at some positions between lens units 24 constituting the relay lens system 23 as illustrated as positions L3, L4 in FIG. 1 besides the above position. The focus position shift member 25 may be arranged at any position of other image formation surfaces in the lens barrel unit 11. Further, the focus position shift member 25 may be arranged in plural.

Also, in the above embodiment, though the focus position shift member 25 has the hollow cylindrical shape, the shape thereof may be a hollow conical shape such that the light passing through the focus position shift member 25 diffuses. Further, a plurality of chip shaped members may be arranged as the focus position shift member 25. Furthermore, in the above embodiment, as illustrated in FIG. 3, though the time sequential process is performed such that the imaging processes of red color, blue color and green color are performed by time division and the color video signals are generated by image composition, the invention is not limited to such a time sequential process. Finally, though the LEDs are used as the coaxial illumination unit 32, incandescent type lamps such as xenon lamps or cold cathode ray lamps may be used.

REFERENCE NUMERALS

1: rigid endoscope 11: lens barrel unit 12: camera unit 21: object lens 22: ocular lens 23: relay lens system 24: lens unit 25: focus position shift member 31: image sensor 32 coaxial illumination unit 33a, 33b, 33c: LED 41: camera processing unit 42: light source control unit 43: synchronization control unit 44: video signal processing unit 45: memory 46a, 46b, 46c: storage unit 47: monitor

What is claimed is:

1. An endoscope comprising:
   a lens barrel unit that has a relay lens system;
   a camera unit that is connected to a base end side of the lens barrel unit and has an imaging device imaging an object through the relay lens system;
   a coaxial illumination unit that is disposed coaxially with the imaging device to surround the imaging device and illuminates the object through the relay lens system; and
   a focus position shift member that is disposed at one of a plurality of image formation positions in the relay lens system and shifts a focus position of illumination light from the coaxial illumination unit.

2. The endoscope according to claim 1, wherein the lens barrel unit further has an object lens ahead of the relay lens system, and the focus position shift member is disposed between a most-advanced lens unit and the object lens to include a space in front of a backward focus position of the object lens.

3. The endoscope according to claim 1, wherein the focus position shift member has a bundle fiber in a cross-sectional shape corresponding to a light-emitting surface of the coaxial illumination unit.

4. The endoscope according to claim 1, wherein the focus position shift member has a light guide in a cross-sectional shape corresponding to a light-emitting surface of the coaxial illumination unit, and of which refractive index is more than 1.

5. The endoscope according to claim 1, wherein the coaxial illumination unit has a ring-shaped light-emitting diode array having a plurality of light-emitting diodes mixed with at least three primary colors.

* * * * *